United States Patent
Jepsen et al.

(10) Patent No.: US 10,045,132 B2
(45) Date of Patent: Aug. 7, 2018

(54) METHOD OF FITTING A HEARING AID SYSTEM, A HEARING AID FITTING SYSTEM AND A COMPUTERIZED DEVICE

(71) Applicant: WIDEX A/S, Lynge (DK)

(72) Inventors: Morten Love Jepsen, Frederiksberg C (DK); Jesper Theill, Lynge (DE)

(73) Assignee: Widex A/S, Lynge (DK)

( * ) Notice: Subject to any disclaimer, the term of this patent is extended or adjusted under 35 U.S.C. 154(b) by 0 days.

(21) Appl. No.: 15/383,189

(22) Filed: Dec. 19, 2016

(65) Prior Publication Data
US 2017/0180894 A1    Jun. 22, 2017

(30) Foreign Application Priority Data

Dec. 22, 2015   (DK) .................................. 2015 00830

(51) Int. Cl.
   *H04R 25/00*   (2006.01)
   *A61B 5/12*    (2006.01)
   *G06F 3/16*    (2006.01)

(52) U.S. Cl.
   CPC ............. *H04R 25/70* (2013.01); *A61B 5/123* (2013.01); *H04R 25/356* (2013.01); *G06F 3/162* (2013.01)

(58) Field of Classification Search
   CPC ...... H04R 25/70; H04R 25/356; A61B 5/123; G06F 3/162
   USPC ........................................................ 600/559
   See application file for complete search history.

(56) References Cited

U.S. PATENT DOCUMENTS

| 4,139,730 A | 2/1979 | Franklin |
| 2001/0049480 A1* | 12/2001 | John ................... A61B 5/04845 600/559 |
| 2002/0076056 A1 | 6/2002 | Pavlakos |
| 2007/0156063 A1* | 7/2007 | Zoth ..................... A61B 5/121 600/559 |
| 2010/0268115 A1 | 10/2010 | Wasden et al. |
| 2015/0023512 A1 | 1/2015 | Shennib |

FOREIGN PATENT DOCUMENTS

WO     2008/109491 A1    9/2008

OTHER PUBLICATIONS

Danish Search Report for Patent Application No. PA 2015 00830 dated Apr. 14, 2016.
International Search Report cited in PCT/EP2016/080281 dated Feb. 24, 2017.

* cited by examiner

Primary Examiner — Sunita Joshi
(74) Attorney, Agent, or Firm — Sughrue Mion, PLLC

(57) ABSTRACT

A method (100) of fitting a hearing aid system comprising identification of an auditory neurodegeneration of a person based on the ability of the person to perceive small differences in intensity level, a computerized device (200, 300) and a non-transitory computer-readable medium storing instructions thereon, which when executed by a computer perform said method.

9 Claims, 2 Drawing Sheets

METHOD OF FITTING A HEARING AID SYSTEM, A HEARING AID FITTING SYSTEM AND A COMPUTERIZED DEVICE

This application is based on and claims priority from Danish application PA201500830 filed Dec. 22, 2015, the contents of which are incorporated by reference herein.

The present invention relates to a method of fitting a hearing aid system and a hearing aid fitting system. The present invention also relates to a computerized device configured to identifying an auditory neurodegeneration of a person. The present invention furthermore relates to a computer-readable storage medium having computer-executable instructions, which when executed carry out the method of identifying an auditory neurodegeneration of a person.

BACKGROUND OF THE INVENTION

Generally a hearing aid system according to the invention is understood as meaning any system which provides an output signal that can be perceived as an acoustic signal by a user or contributes to providing such an output signal, and which has means which are used to compensate for an individual hearing deficiency of the user or contribute to compensating for the hearing deficiency of the user. These systems may comprise hearing aids which can be worn on the body or on the head, in particular on or in the ear, and can be fully or partially implanted. However, some devices whose main aim is not to compensate for a hearing deficiency may also be regarded as hearing aid systems, for example consumer electronic devices (televisions, hi-fi systems, mobile phones, MP3 players etc.) provided they have, however, measures for compensating for an individual hearing deficiency.

Within the present context a hearing aid may be understood as a small, battery-powered, microelectronic device designed to be worn behind or in the human ear by a hearing-impaired user.

Prior to use, the hearing aid is adjusted by a hearing aid fitter according to a prescription. The prescription is conventionally based on a hearing test that measures the hearing threshold, resulting in a so-called audiogram, of the performance of the hearing-impaired user's unaided hearing. The prescription may be developed to reach a setting where the hearing aid will alleviate a hearing deficiency by amplifying sound at frequencies in those parts of the audible frequency range where the user suffers a hearing deficit in the form of an elevated hearing threshold.

A hearing aid comprises one or more microphones, a battery, a microelectronic circuit comprising a signal processor, and an acoustic output transducer. The signal processor is preferably a digital signal processor. The hearing aid is enclosed in a casing suitable for fitting behind or in a human ear. For this type of traditional hearing aids the mechanical design has developed into a number of general categories. As the name suggests, Behind-The-Ear (BTE) hearing aids are worn behind the ear. To be more precise, an electronics unit comprising a housing containing the major electronics parts thereof is worn behind the ear and an earpiece for emitting sound to the hearing aid user is worn in the ear, e.g. in the concha or the ear canal. In a traditional BTE hearing aid, a sound tube is used to convey sound from the output transducer, which in hearing aid terminology is normally referred to as the receiver, located in the housing of the electronics unit and to the ear canal. In some modern types of hearing aids a conducting member comprising electrical conductors conveys an electric signal from the housing and to a receiver placed in the earpiece in the ear. Such hearing aids are commonly referred to as Receiver-In-The-Ear (RITE) hearing aids. In a specific type of RITE hearing aids the receiver is placed inside the ear canal. This category is sometimes referred to as Receiver-In-Canal (RIC) hearing aids. In-The-Ear (ITE) hearing aids are designed for arrangement in the ear, normally in the funnel-shaped outer part of the ear canal. In a specific type of ITE hearing aids the hearing aid is placed substantially inside the ear canal. This category is sometimes referred to as Completely-In-Canal (CIC) hearing aids. This type of hearing aid requires an especially compact design in order to allow it to be arranged in the ear canal, while accommodating the components necessary for operation of the hearing aid.

Within the present context a hearing aid system may comprise a single hearing aid (a so called monaural hearing aid system) or comprise two hearing aids, one for each ear of the hearing aid user (a so called binaural hearing aid system). Furthermore the hearing aid system may comprise an external device, such as a smart phone having software applications adapted to interact with other devices of the hearing aid system, or the external device alone may function as a hearing aid system. Thus within the present context the term "hearing aid system device" may denote a traditional hearing aid or an external device.

It is well known for persons skilled in the art of hearing aid systems that some hearing aid system users are not satisfied with results of conventional hearing-aid fitting that primarily is based on measuring an elevated hearing threshold.

A subgroup of potential hearing aid users are assumed to have auditory-nerve dysfunction due to aging or ototoxic drug exposure or noise trauma. This type of hearing deficit may also be denoted auditory neurodegeneration. Measurement of the hearing threshold cannot generally be used to diagnose this type of hearing deficiency. Many hearing aid fitters may therefore be hesitant to suggest or apply potentially beneficial sound-processing features specifically adapted to relieve an auditory neurodegeneration, unless a hearing aid fitting system capable of detecting an auditory neurodegeneration is available.

It is therefore a feature of the present invention to provide a hearing aid fitting system or some other computerized device capable of detecting an auditory neurodegeneration.

Such a measure may also detect hearing deficiencies for those persons that complain about a problem with understanding speech in noise, but do not reveal an elevated hearing threshold (that may also be denoted reduced pure-tone sensitivity). Today, these persons are not prescribed hearing-aid system treatment and are therefore left to live with their hearing deficit.

According to another aspect it is a feature of the present invention to suggest a method of fitting a hearing aid system that comprises detection of an auditory neurodegeneration in manner that is time-efficient and easy to execute such that it may be suitable for implementation as part of a standard hearing aid fitting procedure.

It is another feature of the present invention to provide a computerized device capable of suggesting and/or providing features specifically directed at relieving an auditory neurodegeneration.

SUMMARY OF THE INVENTION

The invention, in a first aspect, provides a method of fitting a hearing aid system comprising the steps of: providing a first test sound at a first intensity level; amplitude modulating the first test sound or adding a second test sound with a second intensity level; prompting a person to identify an intensity level difference based on the amplitude modulation of the first test sound or based on a comparison of the intensity level of the first and second test sound respectively; receiving an input from the person in response to said prompting; determining the person's ability to perceive small differences in intensity level based on the input from the person; identifying an auditory neurodegeneration for the person if the ability to perceive small differences in intensity level is reduced compared to the ability of normal hearing persons; and setting a gain or a hearing aid parameter or selecting a hearing aid feature based on the result of said identification.

The invention, in a second aspect, provides a non-transitory computer-readable medium storing instructions thereon, which when executed by a computer perform a method comprising the steps of: providing a first test sound at a first intensity level; amplitude modulating the first test sound or adding a second test sound with a second intensity level; prompting a person to identify an intensity level difference based on the amplitude modulation of the first test sound or based on a comparison of the intensity level of the first and second test sound respectively; receiving an input from the person in response to said prompting; determining the person's ability to perceive small differences in intensity level based on the input from the person; identifying an auditory neurodegeneration for the person if the ability to perceive small differences in intensity level is reduced compared to the ability of normal hearing persons; and setting a gain or a hearing aid parameter or selecting a hearing aid feature based on the result of said identification.

The invention, in a third aspect, provides a computerized device comprising an electro-acoustical output transducer, a graphical user interface, and a software application, wherein the computerized device is adapted to: provide a first test sound at a first intensity level; amplitude modulate the first test sound or adding a second test sound with a second intensity level that is different from the first intensity level; prompt a person to identify an intensity level difference based on the amplitude modulation of the first test sound or based on a comparison of the first and second test sound; receive an input from the person in response to said prompting; determine the person's ability to perceive small differences in intensity level based on the input from the person; and identify an auditory neurodegeneration for the person if the ability to perceive small differences in intensity level is reduced compared to that of normal hearing persons.

Further advantageous features appear from the dependent claims.

Still other features of the present invention will become apparent to those skilled in the art from the following description wherein the invention will be explained in greater detail.

BRIEF DESCRIPTION OF THE DRAWINGS

By way of example, there is shown and described a preferred embodiment of this invention. As will be realized, the invention is capable of other embodiments, and its several details are capable of modification in various, obvious aspects, all without departing from the invention. Accordingly, the drawings and descriptions will be regarded as illustrative in nature and not as restrictive. In the drawings.

DETAILED DESCRIPTION

Within the present context the term software application may be construed to comprise a program storage for storing an executable program, and a processor for executing said program. However, the term software application may also be construed to mean a non-transitory computer readable medium carrying instructions that may be executed by a computer.

Decades ago (1950's) the so-called "short-increment sensitivity index" (SISI) test was introduced, and used for some years, assuming that an increased sensitivity to intensity differences at low sound levels would indicate a cochlear (typically outer-hair cell) loss due to loudness recruitment. However, the SISI test did not gain wider usage, which may be due to the missing ability to reliably indicate cochlear loss, and due to the fact that no direct use of the result in hearing-aid fitting was found.

The present invention is based on a test that in some aspects is similar to the SISI test, but in other aspects is basically the opposite and furthermore is used for a whole new purpose, namely for identifying and quantifying an auditory neurodegeneration and in response hereto adapt a hearing aid system to relieve this type of hearing deficit.

The present invention therefore suggests a test based on the ability of a person to perceive small differences in intensity level provided by an amplitude modulated test sound or by two test sounds that primarily differ in intensity level. The inventors have realized that people with auditory nerve degeneration have a reduced sensitivity to intensity level differences, when the test sounds are presented at relatively high intensity levels, presumed to be because this type of hearing deficit results from a reduced number of nerve-fibers, specifically low spontaneous-rate fibers in the auditory nerve system that respond to the relatively high intensity levels. In this context it is noted that the low spontaneous-rate fibers have been shown to be more susceptible to damage compared to the high spontaneous-rate fibers that respond to the low intensity levels.

Normal hearing persons, on the other hand, generally exhibit an increased sensitivity to intensity level differences with increasing intensity level of the test sounds.

The hearing aid fitting systems and computerized devices according to the present invention can therefore be used to identify persons suffering from auditory neurodegeneration and hereby providing information of the hearing deficit beyond the conventional audiogram.

Additionally the disclosed methods of hearing aid fitting are advantageous in that the identification and quantification of an auditory neurodegeneration may be used to prescribe and fit (which in the following may also be denoted to program) alternative methods of operating hearing aid systems, and/or more aggressive noise-reduction algorithms, whereby persons suffering from this hearing deficit may achieve greater benefit from wearing a hearing aid system.

Figure 1:
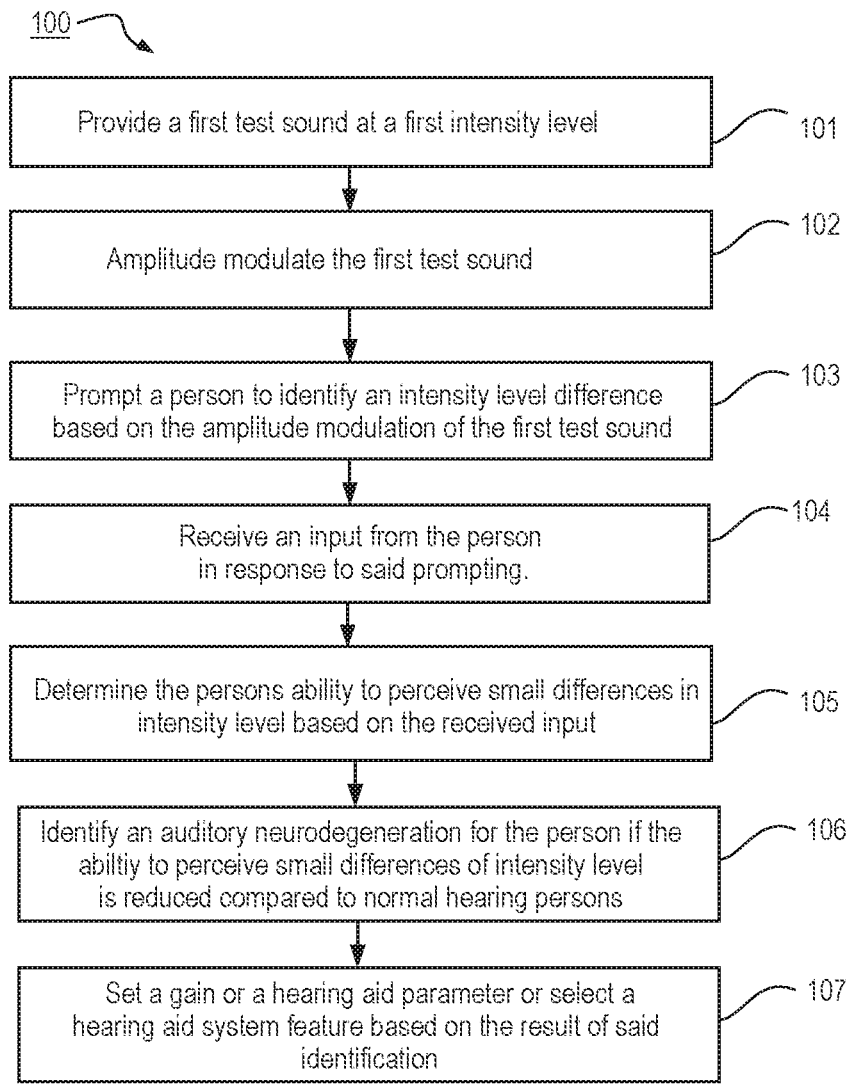
FIG. 1 illustrates highly schematically a method of fitting a hearing aid system according to a first embodiment of the invention.

Reference is first made to FIG. 1, which illustrates highly schematically a method 100 of fitting a hearing aid system according to an embodiment of the invention. The method comprises the steps of:

proving, in a first step 101, a first test sound at a first intensity level;

amplitude modulating, in a second step 102, the first test sound or adding a second test sound with a second intensity level that is different from the first intensity level;

prompting, in a third step 103, a person to identify an intensity level difference based on the amplitude modulation of the first test sound or based on a comparison of the intensity level of the first and second test sound respectively;

receiving, in a fourth step 104, an input from the person in response to said prompting;

determining, in a fifth step 105, the person's ability to perceive small differences in intensity level based on the input from the person;

identifying, in a sixth step 106, an auditory neurodegeneration for the person if the ability to perceive small differences in intensity is reduced compared to the ability of normal hearing persons; and setting, in a seventh step 107, a gain or a hearing aid parameter or selecting a hearing aid feature based on the result of said identification.

Preferably the first intensity level is selected from the range of intensity levels that are covered by the low spontaneous-rate fibers of the auditory nerve, and according to the present embodiment this range of intensity levels is estimated to span the range from 0 dB HL and up to the uncomfortable level for the person. However, it is worth noting that any choice of first intensity level may provide an identification of an auditory neurodegeneration, namely if the ability to perceive small differences in intensity level is reduced compared to that of normal hearing persons.

According to the embodiment of FIG. 1 the magnitude of the increase of the first test sound intensity level due to the amplitude modulation may be selected from the range between 0.5 and 6 dB. In a variation the magnitude of the increase of the first test sound intensity level is selected from the range between 1.5 and 2.5 dB.

According to the embodiment of FIG. 1 the amplitude modulation of the first test sound comprises a first plurality of recurring and time limited increases of the first test sound intensity level, wherein the duration of the time limited increases is around 100 milliseconds or in the range between 25 and 200 milliseconds.

Furthermore, according to the embodiment of FIG. 1, the step of identifying an auditory neurodegeneration for the person if the ability to perceive small differences in intensity level is reduced compared to normal hearing persons comprises the step of determining for the person if a percentage of correct detections, relative to the provided plurality of recurring and time limited increases of the first test sound intensity level, is lower than a first threshold value representing an average percentage of correct detections for a normal hearing person. In a specific variation this first threshold value may be set to 30% correct detections. However, in variations the first threshold value may be selected from a range between 10% and 40% correct detections. In a further variation the average percentage of correct detections for a normal hearing person is provided by subjecting a plurality of normal hearing persons to the disclosed test for determining the ability to perceive small differences in intensity level.

It is another specific advantage of the FIG. 1 embodiment that the percentage of correct answers may be used to quantify the severity of the auditory neurodegeneration, which is particularly advantageous when setting a gain or hearing aid parameter or selecting a hearing aid feature.

In a variation of the first embodiment the determination of the person's ability to perceive small differences in intensity level is based on the input from the person for a multitude of different first intensity levels of the first test sound, and an auditory neurodegeneration for the person being identified if the ability to perceive small differences in intensity level decreases with increasing intensity level of the first test sound. This advantageously simple criteria may be applied because the ability to perceive small differences in intensity level generally increases with increasing intensity level of the first test sound for normal hearing persons, while the inventors have realized that a person suffering from an auditory neurodegeneration generally will exhibit a decreased ability to perceive small differences in intensity level with increasing intensity level of the first test sound.

In another variation of the first embodiment the first test sound is not amplitude modulated. Instead a second test sound is added with a second intensity level, and in order to identify an intensity level difference the person is prompted to compare the intensity level of the first and second test sounds respectively. According to a further variation this may be carried out by varying the second intensity level until the difference, between the first and the second intensity levels, is just noticeable for the person.

Figure 2:
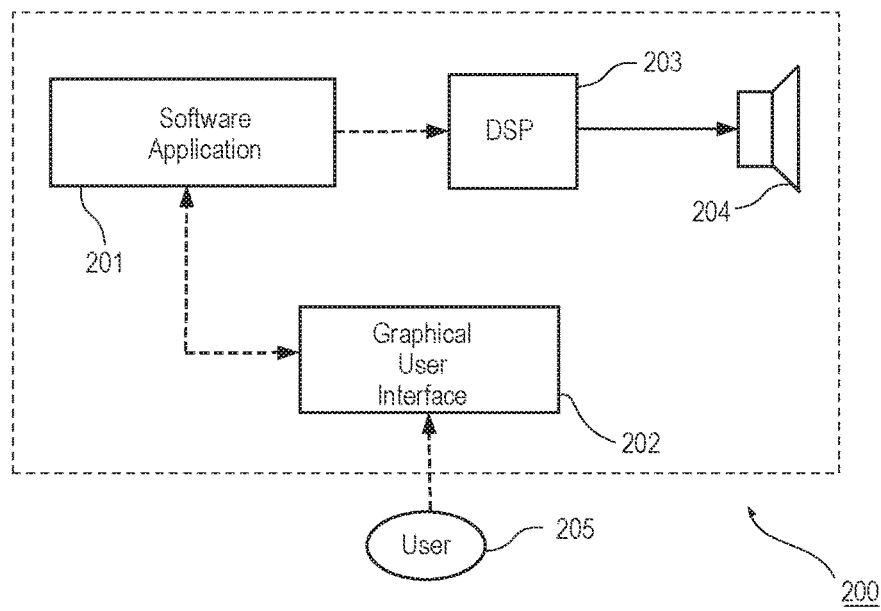
FIG. 2 illustrates highly schematically a computerized device according to an embodiment of the invention.

Reference is now made to FIG. 2, which illustrates highly schematically a computerized device 200 according to an embodiment of the invention. The computerized device 200 comprises a software application 201, a graphical user interface 202, a digital signal processor (DSP) 203 and an electro-acoustical output transducer 204.

FIG. 2 illustrates how a person 205 through the graphical user interface 202 may communicate interactively with the computerized device 200 in a manner controlled by the software application 201. The software application 201 is furthermore adapted to interact with the DSP 203 such that the electro-acoustical transducer 204 can be used to provide a desired acoustical test signal.

In correspondence with the first embodiment according to FIG. 1 the computerized device 200 is adapted to provide a first test sound, using the electro-acoustical output transducer 204, at a first intensity level, wherein the first test sound is amplitude modulated with a first plurality of recurring and time limited increases of the first test sound intensity level.

Furthermore the computerized device 200 is adapted to prompt a person to respond each time one of said plurality of recurring and time limited increases of the first test sound intensity level is detected and adapted to receive, through the graphical user interface, an input from the person in response to said prompting, wherein said input represents the person's ability to perceive one of said plurality of recurring and time limited increases of the first test sound intensity level.

Finally the computerized device 200 is adapted to identify an auditory neurodegeneration for the person if a percentage of correct detections, relative to the first plurality of provided recurring and time limited increases of the test sound intensity level is lower than a first predetermined threshold.

In a specific variation the percentage of correct answers may be used as input to a hearing aid fitting system, whereby parameters of alternative processing features directed specifically at relieving an auditory neurodegeneration may be set dependent on the severity of the auditory degeneration.

In a variation the computerized device 200 is adapted to provide a second test sound with a second intensity level that is different from the first intensity level of the first test sound, and to prompt a person to respond, using the graphical user interface, whether the difference between the first and the second intensity levels is noticeable for the person. Therefore the computerized device 200 is additionally adapted to vary up and down the second intensity level, based on the response from the person, until the difference, between the first and the second intensity levels, is perceived as just noticeable by the person. Furthermore the computerized device 200 is adapted to identify an auditory neurodegeneration if the difference, perceived by the person as just noticeable, is above a second predetermined threshold that is in the range between 1.5 dB and 6 dB. In a further variation the magnitude of the just noticeable difference may be used as input to a hearing aid fitting system, whereby parameters of alternative processing features directed specifically at relieving an auditory neurodegeneration may be set dependent on the severity of the auditory degeneration.

In a further variation an amplitude modulated test signal may also be used to determine just noticeable intensity differences.

In further variations the computerized device 200 is adapted to be part of a conventional hearing aid fitting system, wherein the person to be tested is exposed to the test sounds from loudspeakers controlled by the computerized device and wherein the person responds by signaling his response to a hearing care professional (who may also be denoted a hearing aid fitter) who subsequently inputs the responses to the computerized device. In a more specific variation the computerized device controls at least one hearing aid worn by the person, whereby the test sounds can be provided by the hearing aids.

Figure 3:
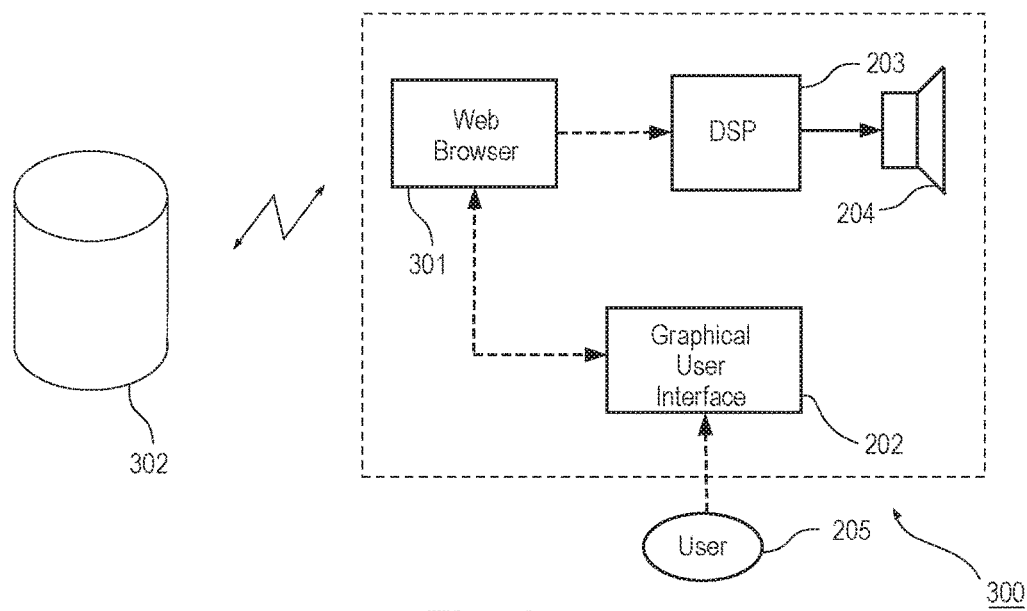
FIG. 3 illustrates highly schematically a computerized device and an external server according to an embodiment of the invention.

Reference is now made to FIG. 3, which illustrates highly schematically a computerized device 300 and an external server 302 according to an embodiment of the invention. The computerized device 300 comprises basically the same elements as the computerized device 200 from the embodiment of FIG. 2, except in so far that the functionality, which in the embodiment of FIG. 2 is provided by the software application 201, in the embodiment of FIG. 3 is provided by a web service that is hosted on the external server 302 and may be accessed using the web browser 301.

In variations of the FIGS. 2 and 3 embodiments the computerized device may be a smart phone, a tablet computer, a portable personal computer or a stationary personal computer. According to the embodiments of FIG. 2 and FIG. 3 the electro-acoustical transducer 204 is a traditional loudspeaker. However, the loudspeaker provides the acoustical test signal to both ears simultaneously, which may be less advantageous in some cases, e.g. if the person only has a hearing deficit in one ear. In variations the software application is therefore set up to provide an acoustical test signal that is selectively provided to either the left ear or the right ear using a set of standard headphones, earphones or even hearing aids connected to the computerized device.

It is a specific advantage of the present invention that it provides a quantitative measure of the auditory neurodegeneration, that may be used to select the most appropriate processing for the person. As one example a person scoring a very low percentage of correct detections, which indicates a serious auditory neurodegeneration, may benefit from more aggressive noise reduction algorithms or alternative processing schemes (which may also be denoted hearing aid features) directed at relieving the amount of sound that the auditory nerves are exposed to. Examples of such alternative hearing aid features comprise frequency contrast enhancement and interleaved frequency band processing.

The method of frequency contrast enhancement in a hearing aid system may be described by the steps of:
   providing an electrical input signal representing an acoustical signal from an input transducer of the hearing aid system;
   splitting the input signal into a first plurality of frequency bands;
   determining a measure of the signal variability for each band of a second plurality of frequency bands;
   determining a threshold level based on the determined measures of the signal variability for each band of the second plurality of frequency bands;
   applying a first gain to a frequency band based on an evaluation of the determined measure of the signal variability for said frequency band relative to the threshold level;
   combining the first plurality of frequency bands into an electrical output signal; and
   using the electrical output signal for driving an output transducer of the hearing aid system.

The method of interleaved frequency band processing in a hearing aid system may be described by the steps of:
   providing an electrical input signal representing an acoustical signal from an input transducer of the hearing aid system;
   splitting the input signal into a plurality of frequency bands;
   forming a first group of frequency bands and a second group of frequency bands, wherein the first group of frequency bands comprises frequency bands that are interleaved with respect to frequency bands comprised in the second group of frequency bands;
   alternating between selecting the first group of frequency bands or the second group of frequency bands;
   processing the selected frequency bands in a first manner, hereby providing processed selected frequency bands;
   processing the non-selected frequency bands in a second manner such that the non-selected frequency bands are attenuated relative to the selected frequency bands, hereby providing processed non-selected frequency bands;
   providing an output signal based on the processed selected and non-selected frequency bands; and
   using the output signal to drive an output transducer of the hearing aid system.

In a further variation of the embodiments of the present invention the percentage of correct answers is used as a measure of the severity of the auditory degeneration and consequently used as input to a hearing aid fitting system, whereby parameters of alternative processing features directed specifically at relieving an auditory neurodegeneration may be set dependent on the severity of the auditory degeneration.

In a specific variation of the FIG. 1 embodiment the final method step of setting a gain or a hearing aid parameter or selecting a hearing aid feature may be omitted. Hereby a method of diagnosing an auditory neurodegeneration results.

Generally the embodiments according to FIGS. 1-3 and their variations may be implemented based on a computer-readable storage medium having computer-executable instructions, which when executed carry out the methods disclosed with reference to FIGS. 1-3.

Generally any of the disclosed embodiments of the invention may be varied by including one or more of the variations disclosed above with reference to another of the disclosed embodiments of the invention. Thus the disclosed method embodiment may also be varied by including one or more of the hearing aid system variations.

The invention claimed is:

1. A method of fitting a hearing aid system comprising the steps of:
   providing a first test sound at a first intensity level;
   creating multiple intensity levels by amplitude modulating the first test sound or adding a second test sound with a second intensity level;
   prompting a person to identify an intensity level difference based on the amplitude modulation of the first test sound or based on a comparison of the intensity level of the first and second test sound respectively;
   receiving an input from the person in response to said prompting;
   determining the person's ability to perceive small differences in intensity level based on the input from the person;
   identifying an auditory neurodegeneration for the person if the ability to perceive small differences in intensity level is reduced compared to the ability of normal hearing persons; and
   setting a gain or a hearing aid parameter or selecting a hearing aid feature based on the result of said identification;
   wherein, when said step of creating multiple intensity levels is by amplitude modulating the first test sound, the step of amplitude modulating the first test sound comprises the step of adding to the first test sound a first plurality of recurring and time limited increases of the first test sound intensity level, and the step of prompting said person to identify an intensity level difference based on the amplitude modulation comprises the further step of prompting the person to respond each time one of said plurality of recurring and time limited increases of the first test sound intensity level is detected; and the step of identifying an auditory neurodegeneration for the person if the ability to perceive small differences in intensity is reduced compared to that of normal hearing persons comprises the step of identifying an auditory neurodegeneration for the person if a percentage of correct detections, relative to the first plurality of provided recurring and time limited increases of the test sound intensity level, is lower than a first predetermined threshold; and
   wherein, when said step of creating multiple intensity levels is by adding a second test sound with a second intensity level, (i) the step of adding a second test sound with a second intensity level that is different from the first intensity level comprises the step of varying the second intensity level until the difference, between the first and the second intensity levels, is just noticeable for the person, (ii) a graphical user interface is adapted in order to allow the person to vary the second intensity level until the difference between the first and the second intensity levels is perceived by the user as just noticeable; and (iii) the step of identifying an auditory neurodegeneration for the person if the ability to perceive small differences in intensity level is reduced compared to the ability of normal hearing persons comprises the step of identifying an auditory neurodegeneration if the difference perceived by the person as just noticeable, is above a second pre-determined threshold, and wherein said second pre-determined threshold is larger than 1.5 dB or in the range between 1.5 dB and 6 dB.

2. The method according to claim 1, comprising the steps of:
   determining the person's ability to perceive small differences in intensity level based on the input from the person for a multitude of different first intensity levels of the first test sound; and
   identifying an auditory neurodegeneration for the person if the ability to perceive small differences in intensity level decreases with increasing level of the first test sound.

3. The method according to claim 1, wherein the increase of the first test sound intensity level is in the range between 0.5 and 6 dB.

4. The method according to claim 1 or 2, wherein the second intensity level differs from the first intensity level with a difference in the range between 0.5 and 6 dB.

5. A method of fitting a hearing aid system comprising the steps of:
   providing a first test sound at a first intensity level;
   amplitude modulating the first test sound or adding a second test sound with a second intensity level;
   prompting a person to identify an intensity level difference based on the amplitude modulation of the first test sound or based on a comparison of the intensity level of the first and second test sound respectively;
   receiving an input from the person in response to said prompting;
   determining the person's ability to perceive small differences in intensity level based on the input from the person;
   identifying an auditory neurodegeneration for the person if the ability to perceive small differences in intensity level is reduced compared to the ability of normal hearing persons; and
   setting a gain or a hearing aid parameter or selecting a hearing aid feature based on the result of said identification;
   wherein the step of adding a second test sound with a second intensity level that is different from the first intensity level comprises the step of varying the second intensity level until the difference, between the first and the second intensity levels, is just noticeable for the person;
   wherein a graphical user interface is adapted in order to allow the person to vary the second intensity level until the difference between the first and the second intensity levels is perceived by the user as just noticeable; and
   wherein the step of identifying an auditory neurodegeneration for the person if the ability to perceive small differences in intensity level is reduced compared to the ability of normal hearing persons comprises the step of identifying an auditory neurodegeneration if the difference perceived by the person as just noticeable, is above a second pre-determined threshold, and wherein said second pre-determined threshold is larger than 1.5 dB or in the range between 1.5 dB and 6 dB.

6. The method according to claim 1, wherein the step of selecting a hearing aid feature based on the result of said identification comprises selecting the hearing aid feature from a group of features comprising: frequency contrast enhancement and interleaved frequency band processing.

7. A non-transitory computer-readable medium storing instructions thereon, which when executed by a computer perform the following method:

providing a first test sound at a first intensity level;
amplitude modulating the first test sound or adding a second test sound with a second intensity level;
prompting a person to identify an intensity level difference based on the amplitude modulation of the first test sound or based on a comparison of the intensity level of the first and second test sound respectively;
receiving an input from the person in response to said prompting;
determining the person's ability to perceive small differences in intensity level based on the input from the person;
identifying an auditory neurodegeneration for the person if the ability to perceive small differences in intensity level is reduced compared to the ability of normal hearing persons; and
setting a gain or a hearing aid parameter or selecting a hearing aid feature based on the result of said identification;
wherein, when said step of creating multiple intensity levels is by amplitude modulating the first test sound, the step of amplitude modulating the first test sound comprises the step of adding to the first test sound a first plurality of recurring and time limited increases of the first test sound intensity level, and the step of prompting said person to identify an intensity level difference based on the amplitude modulation comprises the further step of prompting the person to respond each time one of said plurality of recurring and time limited increases of the first test sound intensity level is detected; and the step of identifying an auditory neurodegeneration for the person if the ability to perceive small differences in intensity is reduced compared to that of normal hearing persons comprises the step of identifying an auditory neurodegeneration for the person if a percentage of correct detections, relative to the first plurality of provided recurring and time limited increases of the test sound intensity level, is lower than a first predetermined threshold; and
wherein, when said step of creating multiple intensity levels is by adding a second test sound with a second intensity level, (i) the step of adding a second test sound with a second intensity level that is different from the first intensity level comprises the step of varying the second intensity level until the difference, between the first and the second intensity levels, is just noticeable for the person, (ii) a graphical user interface is adapted in order to allow the person to vary the second intensity level until the difference between the first and the second intensity levels is perceived by the user as just noticeable; and (iii) the step of identifying an auditory neurodegeneration for the person if the ability to perceive small differences in intensity level is reduced compared to the ability of normal hearing persons comprises the step of identifying an auditory neurodegeneration if the difference perceived by the person as just noticeable, is above a second pre-determined threshold, and wherein said second pre-determined threshold is larger than 1.5 dB or in the range between 1.5 dB and 6 dB.

8. A computerized device, comprising an electro-acoustical output transducer, a graphical user interface, and a software application, wherein the computerized device is adapted to:

provide a first test sound at a first intensity level;
amplitude modulate the first test sound or adding a second test sound with a second intensity level that is different from the first intensity level;
prompt a person to identify an intensity level difference based on the amplitude modulation of the first test sound or based on a comparison of the first and second test sound;
receive an input from the person in response to said prompting;
determine the person's ability to perceive small differences in intensity level based on the input from the person; and;
identify an auditory neurodegeneration for the person if the ability to perceive small differences in intensity level is reduced compared to that of normal hearing persons;
wherein, when said step of creating multiple intensity levels is by amplitude modulating the first test sound, the step of amplitude modulating the first test sound comprises the step of adding to the first test sound a first plurality of recurring and time limited increases of the first test sound intensity level, and the step of prompting said person to identify an intensity level difference based on the amplitude modulation comprises the further step of prompting the person to respond each time one of said plurality of recurring and time limited increases of the first test sound intensity level is detected; and the step of identifying an auditory neurodegeneration for the person if the ability to perceive small differences in intensity is reduced compared to that of normal hearing persons comprises the step of identifying an auditory neurodegeneration for the person if a percentage of correct detections, relative to the first plurality of provided recurring and time limited increases of the test sound intensity level is lower than a first predetermined threshold; and
wherein, when said step of creating multiple intensity levels is by adding a second test sound with a second intensity level, (i) the step of adding a second test sound with a second intensity level that is different from the first intensity level comprises the step of varying the second intensity level until the difference between the first and the second intensity levels is just noticeable for the person, (ii) a graphical user interface is adapted in order to allow the person to vary the second intensity level until the difference between the first and the second intensity levels is perceived by the user as just noticeable; and (iii) the step of identifying an auditory neurodegeneration for the person if the ability to perceive small differences in intensity level is reduced compared to the ability of normal hearing persons comprises the step of identifying an auditory neurodegeneration if the difference perceived by the person as just noticeable, is above a second pre-determined threshold, and wherein said second pre-determined threshold is larger than 1.5 dB or in the range between 1.5 dB and 6 dB.

9. The computerized according to claim 8, wherein the functionality of the software application is provided by an external server hosting a web service adapted to offer the functionality of the software application according to claim 8.

* * * * *